United States Patent [19]

[11] 3,954,845

Martinsson et al.

[45] May 4, 1976

[54] SYNTHETIC DETERGENTS OF THE AMPHOLYTIC BETAINE TYPE, PROCESS FOR PREPARING THE SAME AND COMPOSITIONS

[75] Inventors: Eva Margareta Martinsson, Stenungsund; Karl Martin Edvin Hellsten, Odsmal, both of Sweden

[73] Assignee: Modokemi Aktiebolag, Stenungsund, Sweden

[22] Filed: Nov. 28, 1973

[21] Appl. No.: 419,856

[30] Foreign Application Priority Data

Nov. 30, 1972 Sweden ............................ 15647/72
Nov. 30, 1972 Sweden ............................ 15648/72

[52] U.S. Cl. ....................... 260/501.13; 260/615 R; 260/615 B; 252/527; 252/546; 252/DIG. 7; 252/DIG. 11

[51] Int. Cl.² ........................................ C07C 101/04

[58] Field of Search ........ 260/501.13, 615 B, 584 B

[56] References Cited

UNITED STATES PATENTS

| | | | |
|---|---|---|---|
| 2,217,846 | 10/1940 | Othner et al. | 260/501.13 |
| 2,781,380 | 2/1957 | Mannheimer | 260/501.13 |
| 3,555,079 | 1/1971 | Marumo et al. | 260/501.13 |
| 3,623,988 | 11/1971 | Weimer | 260/615 B |
| 3,636,114 | 1/1972 | Tobler et al. | 260/584 B |
| 3,649,677 | 3/1972 | Morris | 260/501.13 |
| 3,689,470 | 9/1972 | Shachat | 260/501.13 |

*Primary Examiner*—James O. Thomas, Jr.
*Assistant Examiner*—Nicky Chan

[57] ABSTRACT

Synthetic detergents of the ampholytic betaine type are provided, having a 2-hydroxy propylene ether group attached to the nitrogen atom of the betaine; the 2-hydroxy propylene ether group optionally can include a plurality of oxyalkylene units. The process for preparing these betaines easily and inexpensively involves reaction of an alcohol or hydroxy compound with epichlorohydrin to form the corresponding chloroglyceryl ether, which can be aminated and quaternized either in two stages, by reaction of a dialkyl amine and a straight or branched halogenated carboxylic acid, or in one stage by reaction of an amino acid. Detergent compositions containing these betaines are also provided.

11 Claims, No Drawings

SYNTHETIC DETERGENTS OF THE AMPHOLYTIC BETAINE TYPE, PROCESS FOR PREPARING THE SAME AND COMPOSITIONS

Many surface-active ampholytic compounds have been described in the literature. These compounds are generally watersoluble, and have good detergent properties, but they are not widely used as surfactants, and their total volume is probably less than 1% of the total consumption of synthetic detergents. This is explainable largely by the expensive and complicated procedures required to prepare them so that their market price is not competitive. The betaines are usually prepared by reaction of long chain monochlorinated alkyl compounds, but these compounds are difficult to prepare, and therefore rather costly, which is reflected in the market price of the final betaine product.

In accordance with the present invention, surfactants of the ampholytic betaine type are provided which have excellent detergent properties, and are also simple and inexpensive to prepare. The ampholytic betaines in accordance with the invention have the formula:

$$RO(C_{n_1}H_{2n_1}O)_{m_1}(C_{n_2}H_{2n_2}O)_{m_2}(C_{n_3}H_{2n_3}O)_{m_3}CH_2\overset{OH}{\overset{|}{C}}HCH_2\underset{R_1\ \ R_2}{\underset{/\backslash}{N^+}}C_{n_4}H_{2n_4}COO^+$$

wherein:

(1) R represents an aliphatic or cycloaliphatic group having from about six to about twenty-two carbon atoms or an aromatic group linked to the oxygen of the OR group via a carbon of the aromatic nucleus and having from one to six alkyl groups totalling from about four to about eighteen carbon atoms in the alkyl groups, each alkyl group having from one to about eighteen carbon atoms;

2. $R_1$ and $R_2$ are selected from the group consisting of alkyl groups having from one to about three carbon atoms;

3. $n_1$, $n_2$ and $n_3$ represent the number of carbon atoms in each unit, and are within the range from about 2 to about 4;

4. $m_1$, $m_2$ and $m_3$ represent the number of oxyalkylene units, and are within the range from 0 to about 10, it being understood that there can be differing numbers of oxyalkylene groups in various molecules in admixture, and that therefore $m_1$, $m_2$ and $m_3$ represent average numbers, and need not be integers. The sum of $m_1$, $m_2$ and $m_3$ is a maximum of about 10; and 5. $n_4$ represents the number of carbon atoms in the unit, and is within the range from 1 to about 4.

These compounds are quite soluble in water, and have a good detergent effect. The foaming properties can be varied within the range from low foaming to high foaming, according to the number of carbon atoms in the hydrophobic part of the compound. Accordingly, it is possible to prepare detergent compositions containing these ampholytic betaines which have good washing characteristics, and can be adapted to any kind of use. Especially good properties are shown by those ampholytic betaine compounds in accordance with the invention in which both the nitrogen atom and the carboxylic group of the betaine are linked to a single carbon atom, i.e. $n_4$ is 1. Those compounds in which $n_1$, $n_2$ and $n_3$ are 2 and at least one of $m_1$, $m_2$ and $m_3$ is 1 or 2 are preferred, as also are those compounds in which $m_1$, $m_2$ and $m_3$ are 0.

Exemplary R aliphatic groups include alkyl such as hexyl, isohexyl, heptyl, isoheptyl, 2-ethylhexyl, n-octyl, isooctyl, tertiary-octyl, nonyl, isononyl, decyl, undecyl, dodecyl, tridecyl, myristyl, palmityl, stearyl, and eicosyl, as well as alkenyl, dienyl, and trienyl groups such as oleyl, ricinoleyl, linoleyl, linolenyl, decenyl, nonenyl, octenyl, hexenyl and heptenyl.

Exemplary R cycloaliphatic groups include cyclohexyl, cycloheptyl, cyclooctyl, methylcyclohexyl, ethylcyclohexyl, isopropylcyclohexyl, dimethylcyclohexyl, octylcyclohexyl, octadecylcyclohexyl, trimethylcyclohexyl, tetramethylcyclohexyl, diethylcyclohexyl, decylcyclohexyl, dodecylcyclohexyl, myristylcyclohexyl, palmitylcyclohexyl, oleylcyclohexyl, and dodecycyclohexyl.

Exemplary alkyl-substituted aromatic groups include dipropyl phenyl, dibutyl naphthyl, octyl naphthyl, diethyl phenyl, octyl phenyl, dodecyl phenyl, polypropylene phenyl, keryl phenyl, triethyl phenyl, butyl phenyl, dibutyl phenyl, and octadecyl phenyl.

Exemplary oxyalkylene units include oxyethylene, oxypropylene-1,2 and -1,3, and oxybutylene-1,2,-1,4,-2,3, and -1,3. These can be used in combinations of two or three thereof, such as mixed oxyethylene-oxypropylene, oxyethylene-oxybutylene, oxypropylene-oxybutylene, and oxyethylene-oxypropylene-oxybutylene.

Exemplary alkylene units intermediate the nitrogen and carboxylic groups of the betaine include methylene, ethylene, propylene, and 1,2-propylene.

Exemplary $R_1$ and $R_2$ alkyl groups include methyl, ethyl, propyl and isopropyl.

The ampholytic betaines in accordance with the invention can be prepared starting from an aliphatic or cycloaliphatic alcohol having from about six to about twenty-two carbon atoms, where R is aliphatic or cycloaliphatic, or from an aromatic phenol having a total of from about ten to about twenty-four carbon atoms and one or more alkyl groups having a total of from about four to about eighteen carbon atoms in the alkyl groups.

If oxyalkylene units are to be present in the ampholytic betaine, the aliphatic or cycloaliphatic alcohol or aromatic phenol is first reacted with an alkylene oxide selected from the group consisting of ethylene oxide, propylene oxide and butylene oxide and mixtures thereof, to introduce from about one to about ten oxyalkylene units. Propylene oxide-1,3 and propylene oxide-1,2 can be used, as well as butylene oxide-1,3,-1,4, -1,2, -2,3 and -1,3. The condensation product with alkylene oxide contains a terminal hydroxyl group, and is thus reacted in the same manner as the aliphatic or cycloaliphatic alcohol with epichlorohydrin.

The 2-hydroxy propylene group is introduced into this compound by reaction with epichlorohydrin to form the corresponding chloroglyceryl ether. The resulting chloroglyceryl ether can be converted to the betaine either in two stages, by reaction with a dialkyl amine and then a monohalogenated carboxylic acid, or in one stage, by reaction with an amino carboxylic acid. Thus, the preparation is in accordance with the following scheme:

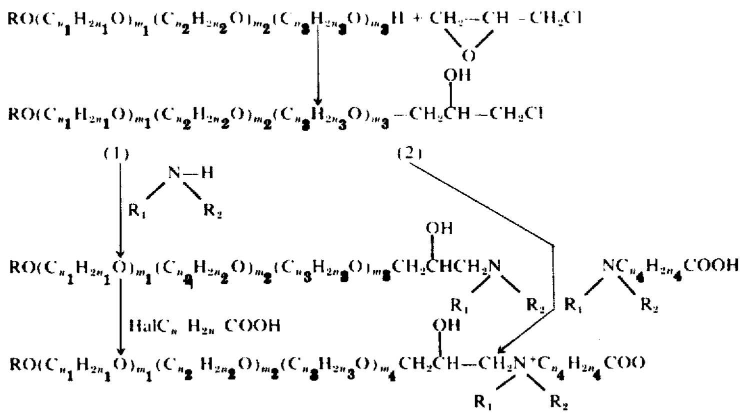

Reaction (2) is preferred, because the reaction product is primarily the ampholytic betaine in accordance with the invention. In reaction (1), the amount of glyceryl ether must be carefully controlled, in order to avoid the production of an undesirable quaternary compound in the reaction between the chloroglyceryl ether and the dialkyl amine.

It is surprising that the amino acid reacts with the chloroglyceryl ether in good yield. Normally, fatty acid chlorides react only slowly with amino acids. It is possible that the chloroglyceryl ether reacts with the amino acid by way of an epoxide intermediate.

The reaction between the hydroxyl compound and the epichlorohydrin is carried out at an elevated temperature with the range from about 100° to about 150°C in the presence of a catlyst. As catalysts, stannic chloride, boron trifluoride and perchloric acid give excellent results, and provide a fast and easily controllable reaction. Other acid catalysts can be used, such as toluene sulphonic acid and sulfuric acid. In order to ensure a quantitative conversion of the hydroxyl compound, the epichlorhydrin can be added in excess.

The reaction between the chloroglyceryl ether and the secondary amine is carried out at an elevated temperature within the range from about 50° to about 150°C in the presence of an alkaline hydroxide catalyst such as an alkali metal hydroxide, for example, sodium hydroxide, potassium hydroxide or lithium hydroxide, or an alkaline earth metal hydroxide, such as calcium hydroxide, barium hydroxide and strontium hydroxide. This reaction can be carried out in the presence of a polar solvent such as water or a low molecular weight alcohol or glycol, such as methanol or ethanol, ethylene glycol, monoethyl ether of ethylene glycol, diethylene glycol, diethyl ether of ethylene glycol, and triethylene glycol.

In order to avoid quaternization of the amine reaction product during the amination, the molar ratio of dialkyl amine to chloroglyceryl ether should be at least 3, and the reaction temperature should not be below about 140°C. The reaction temperature can be reduced to as low as 100°C if even higher molar ratios of dialkyl amine to chloroglyceryl ether are used.

The quaternization of the tertiary amine with the halogenated carboxylic acid is effected in a neutralized aqueous solution, at a reaction temperature within the range from about 50° to about 150°C, for a reaction time within the range from about 2 to about 6 hours. If the tertiary amine is only slightly soluble in water, such as when it contains hydrocarbon groups having more than about fourteen carbon atoms, it may be desirable to add a solvent that is miscible with water, such as ethylene glycol, to increase the solubility of the amine in the reaction mixture, and to lower the viscosity of the reaction mixture.

The reaction of the chloroglyceryl ether with an amino acid is also carried out in an aqueous solution at a temperature within the range from about 50° to about 140°C and for a reaction time within the range from about 15 minutes to about 3 hours. The pH is neutral or slightly basic, within the range from about 7 to about 10. A polar solvent miscible with water also can be added, as in the case of the amination, such as a lower molecular weight alcohol, such as methanol or ethanol, or a glycol such as monoethyl ether of ethylene glycol, diethylene glycol, diethyl ether of ethylene glycol, and ethylene glycol.

In addition to the above reaction procedures, other reactions can be used. Thus, the chloroglyceryl ether can be reacted with ammonia or a primary amine having a methyl or ethyl substituent, and additional alkyl substituents thereupon introduced into the resulting amine, using for example, an alkyl halide such as methyl, ethyl, or propyl chloride, or a dialkyl sulfate such as dimethyl, diethyl or dipropyl sulfate.

It is also possible to use a monoalkyl-substituted amino acid, which is reacted with the chloroglyceryl ether and quaternization of the resulting tertiary amine then carried out with an alkyl halide or dialkyl sulfate, as indicated above. These reactions may however result in a larger amount of by-product, and a lower total yield.

The aliphatic alcohols which can be used in the preparation of the ampholytic betaines according to the invention include hexyl alcohol, isohexyl alcohol, tertiary hexyl alcohol, heptyl alcohol, isoheptyl alcohol, tertiary heptyl alcohol, 2-ethylhexyl alcohol, octyl alcohol, isooctyl alcohol, nonyl alcohol, isononyl alcohol, decyl alcohol, dodecyl alcohol, tetradecyl alcohol, hexadecyl alcohol, and octadecyl alcohol; oleyl alcohol, ricinoleyl alcohol, linoleyl alcohol, and linolenyl alcohol.

Particularly useful are the alcohols and alcohol mixtures derived by hydrogenation from the naturally-occuring fatty acids or fatty acid esters derived from vegetable oils, animal oils, or fats, such as coconut oil, palm oil, soyabeam oil, cottonseed oil, corn oil, castor oil, linseed oil, tallow, grape-seed oil, tung oil, lard safflower seed oil, fish oil and whale oil. Synthetic alcohol mixtures can also be used, prepared according to the Ziegler process or the Oxo process, the latter producing highly branched alcohols and alcohol mixtures.

In addition to the aliphatic alcohols, cycloaliphatic alcohols which can be used include cyclohexanol, cycloheptanol, cyclooctanol, cyclododecanol, cyclohexyldecanol, methylcyclohexanol, diethylcycloheptanol, octadecylcyclooctanol, and decylcyclohexanol.

Alkyl-substituted phenols which can be used include octylphenol, nonylphenol, dodecyl phenol, hexadecyl phenol, dibutylphenol, dioctylphenol and dinonylphenol, keryl phenol, polypropylene phenol, the polypropylene group having from 12 to about 15 carbon atoms, and octadecyl phenol.

Suitable dialkyl amines include dimethylamine, diethylamine, dipropylamine and diisopropylamine.

The halogenated carboxylic acid should be $\alpha$-monohalogenated. Exemplary are monochloroacetic acid, $\alpha$-monochloropropionic acid, and $\alpha$-monochlorobutyric acid.

Aminocarboxylic acids that can be used include glycine, dimethyl glycine, alanine, dimethyl alanine, dimethyl valine, diethyl glycine, ethylpropyl glycine, dipropyl glycine, diethyl alanine, dipropyl alanine, ethypropyl alanine, methylpropyl alanine, diethyl valine, dipropyl valine, and ethylpropyl valine.

The ampholytic betains in accordance with the invention are useful as detergents and surfactants in all kinds of washing compositions, including both liquid and solid compositions, intended for washing and cleaning of any kind of substrate materials, such s textiles, metals, plastics, leather, wood, ceramic, porcelain, stone, glass, china, and painted surfaces, both in the home and in industry, including soap powders and liquid soaps and detergents, shampoos, shaving creams, foaming compositions for the bath, and sanitizing compositions.

In addition to the ampholytic betaine surfactant, the detergent compositions of the invention can also include additional surfactants, including anionic, cationic, and nonionic surfactants. In general, a nonionic surfactant is preferred, in order to impart a desirable low-foaming capacity combined with a good detergent action, but anionic surfactants are also useful adjuncts, if desired in combination with nonionic surfactants, as well.

The anionic sulfate or sulfonate ester surfactants constitue a well known class of anionic surfactants. The alkyl aryl sulfonates are defined by the formula

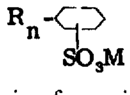

where R is alkyl having from eight to about eighteen carbons, n is a number from one to three, and M is hydrogen on an alkali metal, ammonium or organic amine cation. One example thereof is sodium dodecyl benzene sulfonate.

Another example are the sulfonated phenyl polypropylene alkanes, characterized by the branched chain structure of polypropylene and tertiary alkyl carbon at the benzene ring, and having the following general structure:

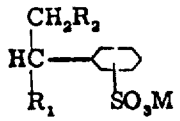

where M is hydrogen, an alkali metal, ammonium, or an organic amine cation, $R_1$ and $R_2$ are alkyl, of the type formula $C_nH_{2n+1}$, and at least one R is a polypropylene group, the whole alkyl group containing preferably twelve to fifteen carbon atoms. These are known compounds, whose preparation and properties are set forth in U.S. Pat. No. 2,477,383, to Lewis, issued July 26, 1949; they are available in commerce under the trade names "Oronite," "Ultrawet," and "Neolene."

Other water-soluble alkyl aromatic sulfonic acids include those prepared by alkylating benzene or napththalene with a kerosene fraction, followed by sulfonation to aromatic sulfonic acids. such as sodium keryl benzene sulfonate.

Another class of useful surfactants are the amidoalkane sulfonates, which are characterized by the following structure:

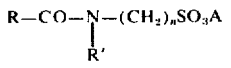

where A is hydrogen or an alkali metal, i.e. ammonium, sodium or potassium, n is a small whole number from 1 to about 5, preferably 2 or 3, R is hydrogen or an alkyl, aryl, or cycloaliphatic group, such as methyl, and R' is an alkyl or alkylene radical, such as myristyl, palmityl, oleyl and stearyl. Sodium palmitic tauride, sodium palmitic methyl tauride, sodium myristic methyl tauride, sodium palmitic stearic methyl tauride, and sodium palmitic methyl amidopropane sulfonate are typical examples thereof.

These compounds are prepared by interacting the corresponding aliphatic acid anhydride or halide with an organic aliphatic aminosulfonic acid, such as taurine, $NH_2CH_2Ch_2SO_3H$, and various N-substituted taurines, such as N-methyl taurine or aminopropane sulfonic acid, $NH_2(CH_2)_3SO_3H$.

Other anionic surfactants include esters of sulfuric acid with aliphatic alcohols of ten to eighteen carbon atoms, particularly oleic acid, tall oil, turkey red oil, and acids derived by the reduction of the fatty acids derived from coconut oil, palm oil, sperm oil and the like long-chain fatty acids, sulfonated castor oil, esters and ethers of isethionic acid, long-chain fatty acid esters and long-chain alkyl ethers of 2,3-dihydroxy-propane sulfonic acid and sulfuric acid esters of monoglycerides and glycerol monoethers.

The nonionic polyoxyalkylene ether, ester and glycol surfactants have the following general formula:

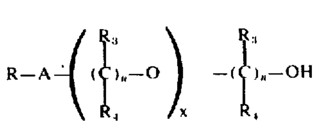

where R is hydrogen or a straight or branched chain saturated or unsaturated hydrocarbon group having from eight to twenty-six carbon atoms or an aralkyl group having a straight or branched chain saturated or unsaturated hydrocarbon group of from six to twenty-four carbon atoms attached to the aryl nucleus, and attached to A through the aryl nucleus, A is selected from the group consisting of ethereal oxygen and sulfur, carboxylic ester and thiocarboxylic ester groups, $R_3$ and $R_3$ are hydrogen or methyl, n is a number from 1 to 4, the total number of carbon atoms in each

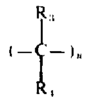

unit is from one to four, and the various

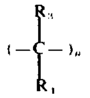

units in the chain can be the same or different, $x$ is a number from 2 to 50. R can, for example, be a straight or branched chain alkyl group, such as octyl, nonyl, decyl, lauryl, myristyl, cetyl, or stearyl, or an alkylaryl group such as octylphenyl, nonylphenyl, decylphenyl, stearylphenyl, etc. In this formula, H could also be replaced by the group - $(C_3H_6O)_mH$, where $m$ is a number ranging from 1 to 10. Examples of such nonionic surfactants are such as have been obtained by adding ethylene oxide, propylene oxide or butylene oxide to the above mentioned alcohols or phenols.

The sulfated alkoxylated derivatives of the above also are useful anionic sulfactants:

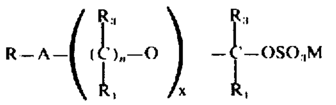

where M is hydrogen or an alkali metal or an organic amine cation, n, x, $R_3$, A and R are as above, the total number of carbon atoms in each

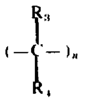

unit is from one to four and the various

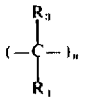

units in the chain can be the same or different.

Where R is alkyl it will be evident that the wetting agent can be regarded as derived from an alcohol, mercaptan, oxy or thio fatty acid of high molecular weight, by condensation with ethylene oxide, propylene oxide or butylene oxide. Typical of this type of alkyl product are the condensation products of oleyl or lauryl (dodecyl) alcohol, or mercaptan, or oleic or lauric acid, with from 8 to 17 moles of ethylene oxide, such as "Emulfor ON." Typical alkyl esters are "Renex" (polyoxyethylene ester of tail oil acids) and "Neutronyl 331" (higher fatty acid ester of polyethylene glycol).

Where R is aralkl, the wetting agent can be derived from an alkyl phenol or thiophenol.

Another class of anionic surfactants are the polyoxyalkylene phosphate esters described by the following formula:

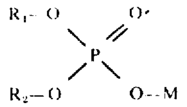

$R_1$ and $R_2$ are alkyl or alkyl phenyl groups having from about eight to about twenty carbon atoms in the alkyl chain, and one of $R_1$ and $R_2$ may also be hydrogen. $R_1$ and $R_2$ can be the same or different.

A preferred class of the phosphate esters are those in which one or both of $R_1$ and $R_2$ is a radical containing a polyoxyalkylene ether group, and no more than one of $R_1$ and $R_2$ is hydrogen. The radical containing polyoxyalkylene ether is of the form:

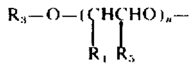

in which n has a value greater than 0, up to about 30, and preferably is within the range from about 1 to about 10, and denotes the average number of oxyalkylene units in the chain. It will be understood that there will be present in admixture species having n values both higher and lower than the average value for n. $R_4$ and $R_5$ are hydrogen, methyl or ethyl.

$R_3$ is a primary or secondary straight or branched chain saturated or unsaturated aliphatic radical having from about ten to about twenty-four carbon atoms, preferably from about twelve to about twenty-to carbon atoms, or a mono, di, or trialkyl-substituted phenyl radical having from about six to about twenty-four carbon atoms, and preferably from about eight to about eighteen carbon atoms in the alkyl portion.

M is hydrogen or a water-soluble salt-forming cation such as an alkali metal, such as, for instance, sodium or potassium; ammonia; or an organic amine, such as an alkanolamine or an alkylamine radical, for example, monoethanolamine, diethanolamine, triethanolamine, butylamine, octalamine, or hexylamine.

These polyoxyalkylene phosphate esters are known compounds, and are described in U.S. Pat. Nos. 3,294,693 and 3,235,627 and the disclosure thereof in these patents is hereby incorporated by reference. Additional polyoxyalkylene phosphate esters are described in U.S. Pat. No. 3,400,148, at column 17, and in the Mayhex and Krupin article in *Soap and Sanitary Chemicals*, referred to above.

Additional polyoxyalkylene phosphate ester surfactants are described in U.S. Pat. No. 3,122,508 to Grifo, Mayhew, Stefcik and Woodward, data Feb. 25, 1964, and in U.S. Pat. Nos. 3,004,056 and 3,004,057 to Nunn and Hesse, dated Oct. 10, 1961.

In general, the polyoxyalkylene ether phosphates are prepared by reaction of phosphorous pentoxide, orthophosphoric acid, pyrosphosphoric acid, or a polyphosphoric acid with a suitable nonionic surfactant base.

In the course of esterification, monoesters and diesters may both be formed, but one may be obtained in preference to the other, according to the reaction conditons and the molar proportions of the reactants. Phosphate esters composed of the mixtures of the mono and di esters in any proportion can be employed, but it is generally preferred that the major proportion, if not all, of the phosphate ester be composed of monoesters.

It may albe be noted that the oxypropylene phosphate esters have a lesser foaming tendency than the oxyethylene phosphate esters, and may be preferred for low foaming compositions. Moreover, the lower the value of n and the higher the number of carbon atoms in the R substituent of the oxyalkylene group, the less the foaming tendency of the phosphate ester.

Exemplary of one class of nonionic surfactants are the alkylene oxide adducts of the formula:

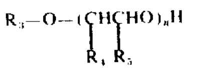

in which *n* has a value greater than 0, up to about 30, and preferably is within the range from about 1 to about 10, and denotes the average number of oxyalkylene units in the chain. It will be understood that there will be present in admixture species having n values both higher and lower than the average value for n. $R_4$ and $R_5$ are hydrogen, methyl or ethyl.

$R_3$ is a primary or secondary straight or branched chain saturated or unsaturated aliphatic radical having from about ten to about twenty-four carbon atoms, preferably from about eight to about thirty carbon atoms derived from a primary alcohol such as octanol, decanol, lauryl alcohol, myristyl alcohol, cetyl alcohol, stearyl alcohol, oleyl alcohol, eicosanol, docosanol, tetracosanol, straight or branched, primary or secondary OXO-alcohols, i.e. alcohols prepared by the OXO process, having from twelve to twenty-six carbon atoms, such as the essentially straight chain alcohols produced from Fischer-Tropsch olefins by the OXO-process, and multi-branched chain alcohols produced from olefins having at least seven carbon atoms and two side chains, such as tripropylene, tetrapropylene, pentapropylene, diisobutylene and triisobutylene by the OXO process, mono, di and trialkyl phenols, such as octyl phenol, isooctyl phenol, nonyl phenol, dodecyl phenol, dioctyl phenol, dinonyl phenol, didodecyl phenol, trioctyl phenol, trihexyl phenol, tridodecyl phenol, methyloctyl phenol, and ethylisononyl phenol, tri-primary, secondary, and tertiary butyl phenol, 3-methyl-4,6-dibutyl phenol, octadecyl phenol, dioctadecyl phenol, trioctadecyl phenol, mono, di and tributyl cresol, mono, di and trinonyl cresol.

The polyoxyalkylene base

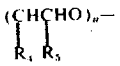

can be polyoxy-1,2-propylene; polyoxyethylene; polyoxy-1,2-butylene; polyoxy-2,3-butylene; the so-called Pluronic type of nonionic surfactants, generally block copolymers of a polyoxyethylene chain and a polymerized alkylene oxide of at least three carbon atoms, preferably 1,2-propylene oxide, ranging in molecular weight from about 300 to about 10,000. Thus, the alkylene oxide condensate may consist entirely of one alkylene oxide, or of a condensed mixture of two or more alkylene oxides, such as a mixture of ethylene oxide and propylene oxide, in blocks, or heterogeneously distributed in the oxyalkylene chain.

A preferred class of nonionic surfactants are the alkoxylated alkyl phenols and thiophenols, which have the following general formula:

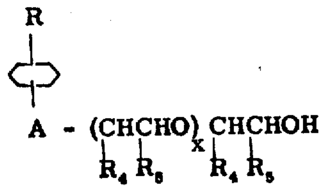

where R is a straight or branched chain saturated or unsatured hydrocarbon group having at least six carbon atoms up to approximately twenty-four carbon atoms, A is oxygen or sulfur, $R_4$ and $R_5$ are hydrogen, methyl or ethyl, and *x* is a number from 5 to 50. R can, for example, be a straight or branched chain octyl, nonyl, decyl, lauryl, cetyl, myristyl, or stearyl group. Typical are the condensation products of octyl and nonyl phenol and thiophenol with from 8 to 17 moles of ethylene oxide, available commercially under the trade name "Igepal CA."

Also useful are the poly-1,2-alkylene oxide wetting agents described and claimed in U.S. Pat. Nos. 2,674,619 to Lundsted, dated Apr. 6, 1954, and No. 2,677,700 to Jackson et al., dated May 4, 1954. These are condensates of 1,2-alkylene oxides, such as 1,2-propylene oxide or 1,2-butylene oxide, alone or in admixture, and such mixtures can also include ethylene oxide, such as the polyoxypropyleneoxyethylene condensates, the ethylene oxide residues constituting from 20 to 90% of the resulting condensate.

These condensates conform to one of the following two type formulae:

$$Y\,[\,(C_3H_6O)_n - E - H\,]_x$$

where Y is the residue of an organic compound containing therein *x* active hydrogen atoms, *n* is an integer, *x* is an integer greater than 1; the values of *n* and *x* are such that the molecular weight by hydroxyl number; E is a polyoxyalkylene chain wherein the oxygen/carbon atom ratio is at least 0.5, and E constitutes 20–90%, by weight, of the compound:

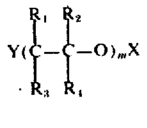

wherein Y is the residue of an organic compound containing therein a single hydrogen atom capable of reacting with a 1,2-alkylene oxide: $R_1$, $R_2$, $R_3$ and $R_4$ are selected from the group consisting of hydrogen, aliphatic radicals and aromatic radicals, at least one such substituent being a radical other than hydrogen; *m* is greater than 6.4 as determined by hydroxyl number, and X is a water-solubilizing group.

Further suitable nonionic surfactants have the general formula:

$$H(OC_2H_4)_{n1}\ 1\ (OC_3H_6)_{m1} - OC_{2\ to\ 3}H_{4\ to\ 6} - O(C_3H_6O)_{m2} - (C_2H_4O)_{n2} - H$$

wherein $m_1$ and $m_2$ are numbers ranging from 10 to 50, and $n_1$ and $n_2$ are numbers ranging from 1 to 50. Examples of surfactants according to this formula are block copolymers of ethylene oxide and propylene oxide based on propylene glycol and having added to them propylene oxide up to a molecular weight of 1000 to 3000, after which ethylene oxide has been added to cause the proportion of ethylene oxide to constitute 5 to 80- of the molecular weight of the compound. In addition to the surfactants, the detergent compositions of the invention can include other components which are customary in detergent compositions, such as corrosion inhibitors, alkaline builder salts, neutral builder salts, soil-suspending agents, optical brightening agents, coloring agents and pigments, perfumes, foam suppressants, and biocidal agents.

Alkaline inorganic and organic builder salts or sequestrants are added in order to improve soil-removal power, particularly for heavily soiled articles. The amount of the alkaline builder salt is usually within the range from about 10 to about 80% by weight of the total solids of the composition, preferably from 20 to 60% by weight. The alkali metal polyphosphates are particularly advantageous in contributing heavy duty performance and in improving detergent properties in hard water. Such polyphosphates include pentasodium triipolyphosphate, sodium acid tripolyphosphate, pentapotassium tripolyphosphate, tetrasodium and tetrapotassium pyrophospshate, sodium tetraphosphate, sodium hexametaphosphate, and pentaammonium tripolyphosphate.

The alkali metal silicates, borates, and carbonates also can be employed, alone or in admixture with polyphosphates, as alkaline builder salts. Examples are the sodium metasilicates, borax, and sodium carbonate, and urea.

Also useful are chelating or sequestering agents. These include the alkali metal, ammonium, and organic amine salts of polyamino-carboxylic acids, for example, the mono, di, tri and tetrasodium salts of ethylene diamine tetraacetic acid, the mono, di and trisodium salts of nitrilo-triacetic acid, and the sodium salts of hexamethylene diamine tetraacetic acid, hydroxyethyl ethylenediamine triacetic acid, hydroxyethyl diimino-diacetic acid, and diethylene triamine pentaacetic acid; salts of oxycarboxylic acids, such as citric acid, oxydiacetic acid, and gluconic acid; and salts of unsaturated polycarboxylic acids, such as polymaleic acid, polyitaconic acid and polyacrylic acid. These compounds are characterized by the ability to sequester or form complexes with hardness-forming metal ions in aqueous solutions, and therefore are particularly useful when the detergent composition is to be employed in water of medium or heavy hardness. The amount of chelating agent or sequestrant is generally within the range from about 5 to about 40%, but preferably from about 10 to about 30% by weight of the composition.

Neutral builder salts such as sodium sulfate and potassium sulfate are formed in the neutralization of the sulfate or sulfonate ester detergents and are usually present in admixture with such detergents. Additional amounts of such sulfates can be added, if desired, to build or extend the composition.

Other additives are bleaching agents, such as sodium perborate, sodium percarbonate, sodium perpyrophosphate and potassium persulfate; fatty acid soap, sodium aluminate and sodium zincatte, wetting agents; textile softeners; perfumes, etc.

Soil-suspending agents also can be added, particularly for heavy duty formulations. Suitable soil-suspending agents are sodium carboxymethyl cellulose, sodium cellulose sulfate, lower alkyl and hydroxyalkyl cellulose ethers, such as ethyl hydroxyethyl cellulose, ethyl hydroxypropyl cellulose, hydoxyethyl cellulose, as well as polyvinyl alcohol and polyvinylpyrrollidone. Soil-suspending agents are usually used, if at all, in amounts of from about 0.05 to about 5%, preferably from 0.1 to 2%, by weight of the total solids.

Optical brightening agents that may be used include stilbenes, diamino-stilbene, acylated cyanuric and triazalyl derivatives of stilbenes, diphenyl derivates, dibenzothiophene derivatives, aminocoumarone salts, derivatives of azotized amino-containing benzoxazoles, benzothiazoles, and benzimidazoles. A number of such agents are disclosed in U.S. Pat. No. 3,122,508.

The compositions of the invention can be used for washing and cleaning a variety of materials, such as textiles, metals, plastics, leather, wood, stone, glass, porcelain, painted surfaces, and title, both in household and industrial applications.

The following Examples in the opinion of the inventor represent preferred embodiments of the invention.

EXAMPLE 1

Into a glass flask provided with stirrer, heating means and reflux condenser was introduced 200 grams (1 mol) of a mixture of 55% lauryl alcohol and 45% myristyl alcohol. The alcohols were heated to 75°C, and there was then added 2 grams of stannic chloride $SnCl_4$ and 101 grams (1.1 mol) of epichlorohydrin over a period of about 1 hour. The temperature was then raised to 125°C, with continued stirring, and the mixture held at this temperature for 2 hours. Residual epichlorohydrin was removed by vacuum distillation. The residual product was a slightly yellow liquid.

To this product there was added 1200 ml of a 14% solution of dimethylamine in ethanol, corresponding to 3 mols of dimethylamine. The resulting mixture was then heated to 150°C in an autoclave, with stirring, and held at this temperature for 1 hours. The reaction mixture was then cooled, and 40 grams (1 mol) of sodium hydroxide was added. Excess dimethylamine and the ethanol were then separated by vacuum distillation at 50°C. The product obtained was analyzed by titration with perchloric acid in glacial acetic acid, and was found to contain solely the mixed lauryl-myristyl oxy-2-hydroxy propylene dimethlamine.

One part by weight of this product, corresponding to 0.5 mol tertiary amine, was stirred into 6 parts by weight of water, and the solution brought to 70°C. Then, at 70°C over 5 minutes 0.6 mol monochloroacetic acid was added, in the form of a 20% aqueous solution neutralized with sodium hydroxide to pH 7. The reaction was allowed to proceed at 70°C for 2 hours, and was then continued for another 2 hours at 90°C. The course of the reaction was followed by titration of the liberated chloride ions with silver nitrate solution.

At the end of the reaction the product was a clear aqueous solution having good foaming and detergent properties of ampholytic betaine having the formula:

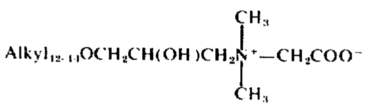

The yield calculated on the amount of added alcohol was 96%.

EXAMPLE 2

Into a glass flask provided with stirrer, heating means and reflux condenser was introduced 200 grams (1 mol) of a mixture of 55% lauryl alcohol and 45% myristyl alcohol. The alcohols were heated to 75°C, and there was then added 2 grams of stannic chloride $SnCl_4$ and 101 grams (1.1 mol) of epichlorohydrin over a period of about 1 hour. The temperature was then raised to 125°C with continued stirring, and the mixture held at this temperature for 2 hours. Residual epichlorohydrin was removed by vacuum distillation. The residual product was a slightly yellow liquid.

To this product there was added 340 grams of a 40% aqueous solution of dimethylamine, corresponding to 3 mols of dimethylamine. The resulting mixture was then heated to 150°C in an autoclave with stirring and held at this temperature for 1 hour. The reaction mixture was then cooled and 40 grams (1 mol) of sodium hydroxide was added. The mixture was allowed to separate in a separatory funnel, and the top phase containing the amine so removed. Excess dimethylamine was then separated by vacuum distillation at 50°C. The product was the mixed lauryl myristyl oxy-2-hydroxy propylene dimethylamine.

One part by weight of this product corresponding to 0.5 mol tertiary amine was stirred into 1.5 parts by weight of water, and then 0.6 mol monochloracetic acid was added at 70°C over 1 hour in the form of a 40% water solution neutralized with sodium hydroxide to pH 7. The reaction was allowed to proceed at 70°C for another hour, and was then continued for 2 hours at 90°C. At the end of the reaction the product was a clear aqueous solution having good foaming and detergent properties of ampholytic betaine having the formula:

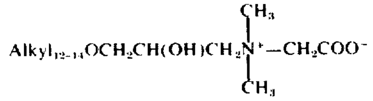

The yield calculated on the amount of added alcohol was 97%.

EXAMPLE 3

Into a glass flask provided with stirrer, heating means and reflux condenser was introduced 418 grams (1 mol) of cetyl tetraoxyethylene alcohol adduct having the formula: $C_{16}H_{33}O(C_2H_4O)_4H$. The alcohol was heated to 75°C, and there was then added 2 grams of stannic chloride and 101 grams (1.1 mol) of epichlorohydrin over a period of about 1 hour. The temperature was then raised to 125°C with continued stirring, and the mixture held at this temperature for 2 hours. Residual epichlorohydrin was then removed by vacuum distillation. The residual product was a slightly yellow liquid.

To 510 grams (1 mol) of this product there was added 340 g of a 40% aqueous solution of dimethylamine, corresponding to 3 mols of dimethylamine. The resulting mixture was then heated to 150°C. in an autoclave with stirring, and held at this temperature for 1 hour. The reaction mixture was then cooled and 40 grams (1 mol) of sodium hydroxide was added. The mixture was allowed to separate in a separatory funnel, and the top phase containing the amine removed. Excess dimethylamine was then separated by vacuum distillation at 50°C. The product obtained was cetyl tetraoxyethylene oxy-2-hydroxy propylene dimethylamine.

One part by weight of this product corresponding to 0.5 mol tertiary amine was stirred into 0.5 part by weight ethylene glycol and one part by weight of water. The mixture was heated to 70°C. and 0.6 mol of monochloracetic acid added at 70°C over 1 hour in the form of a 40% water solution neutralized with sodium hydroxide to pH7. The reaction was allowed to proceed at 70°C for another hour and was then continued for 2 hours at 90°C.

By addition of sodium hydroxide, the pH was maintained between about 9 and 10. The product mixture was fluid and clear. Analysis of the chloride content showed 100% conversion of chloroacetate, and 98% of the tertiary amine had reacted. The product was:

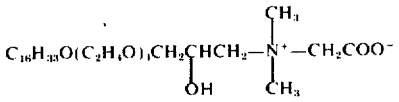

EXAMPLE 4

Into a glass flask provided with stirrer, heating means and reflux condenser was introduced 246 grams (1 mol) of octanol propylene oxide adduct containing 2 mols propylene oxide: $c_8H_{17}O(C_3H_6O)_2H$. The alcohol was heated to 75°C, and there was then added 2 grams of stannic chloride and 101 grams (1.1 mol) of epichlorohydrin over a period of about 1 hour. The temperature was then raised to 125°C with continued stirring, the mixture held at this temperature for 2 hours. Residual epichlorohydrin was then removed by vacuum distillation. The residual product was a slightly yellow liquid.

To 338 grams of this product there was added 340 g of a 40% aqueous solution of dimethylamine, corresponding to 3 mols of dimethylamine. The resulting mixture was then heated to 150°C in an autoclave with stirring, and held at this temperature for 1 hour. The reaction mixture was then cooled and 40 grams (1 mol) of sodium hydroxide was added. The mixture was allowed to separate in a separatory funnel, and the top phase containing the amine removed. Excess dimethylamine was then separated by vacuum distillation at 50°C. The product obtained was octyltetraoxy propylene-oxy-2-hydroxy propylene dimethylamine.

One part by weight of this produce corresponding to 0.5 mol tertiary amine was stirred into 0.5 part by weight diethylene glycol and one part by weight of water. The mixture was heated to 70°C, and 0.6 mol monochloroacetic acid added at 70°C over one hour in the form of a 40% water solution neutralized with sodium hydoxide to pH 7. The reaction was allowed to proceed at 70°C for another hour, and was then continued for 2 hours at 90°C. At the end of the reaction the product was a clear aqueous solution of ampholytic betaine having the formula:

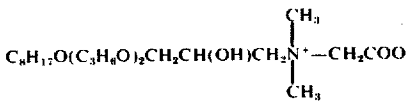

The yield calculated on the amount of added alcohol was 96%.

EXAMPLE 5

Into a glass flask provided with stirrer, heating means and reflux condenser was introduced 308 grams (1 mol) of nonyl phenol-ethylene oxide adduct $C_9H_{19}C_6H_4O(C_2H_4O)_2H$. The alcohol was heated to 75°C and there was then added 2 grams of stannic chloride and 101 grams (1.1. mol) of epichlorohydrin over a period of about 1 hour. The temperature was then raised to 125°C with continued stirring, and the mixture held at this temperature for 2 hours. Residual epichlorohydrin was then removed by vacuum distillation. The residual product was a slightly yellow liquid.

80 grams of this product (0.2 mol) was mixed with 67.5 grams of 40% aqueous solution of dimethylamine (0.6 mol). The reaction mixture was allowed to stand for 2 hours at 150°C. Hydrochloric acid which formed was neutralized with 8.32 grams of sodium hydroxide, after which the mixture was transferred to a separatory funnel, and the top phase containing the tertiary amine was separated.

Dimethylamine dissolved in the tertiary amine phase was removed by vacuum distillation. The product was analyzed by titration with perchloric acid in glacial acetic acid and with sodium lauryl sulfate at pH 11, and was found to consist of 95% tertiary amine, but no quaternary compounds.

58 grams of this tertiary amine was dissolved in 61 grams of water and 26 grams of diethylene glycol. The mixture was heated to 70° C and then a 40% aqueous solution of monochloroacetic acid neutralized with sodium hydroxide was added dropwise over 1 hour, so that the total quantity of monochloroacetic acid added mounted to 15.7 grams. The reaction mixture was then held another hour at 70° C after when the temperature was increased to 90° C and held at this temperature for 3 hours. At the conclusion of this time 97% of the tertiary amine had reacted and 99% of the theoretical amount of chloride ions had formed. The produce had the formula:

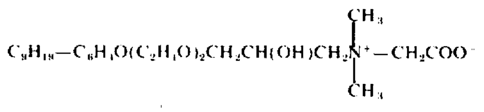

This product had a syrupy consistency at room temperature, and displayed good cleansing properties.

EXAMPLE 6

Into a glass flask provided with stirrer, heating means and reflux condenser was introduced 200 grams (1 mol) of a mixture of 55% lauryl alcohol and 45% myristyl alcohol. The alcohols were heated to 75° C and there was then added 2 grams of stannic chloride and 101 grams (1.1 mol) of epichlorohydrin over a period of about 1 hour. The temperature was then raised to 125° C, with continued stirring, and the mixture held at this temperature for 2 hours. Residual epichlorohydrin was removed by vacuum distillation. The residual product was a slightly yellow liquid.

Sodium dimethylglycine (134 grams) and monoethyleneglycol (344 grams) were mixed, and brought to 125° C, whereupon the chloroglyceryl ether was added dropwise over 25 minutes. The reaction was continued at 125° C for a further ten minutes, and then halted. The mixture, which essentially consisted of sodium chloride and the ampholytic betaine product, was hot-filtered, obtaining a clear yellowish liquid. The conversion of the chloroglyceryl ether with dimethylglycine was 98%. The final product had the formula:

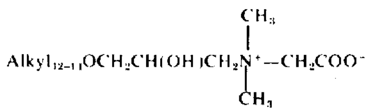

EXAMPLE 7

Into a glass flask provided with stirrer, heating means and reflux condenser was introduced 348 grams (1 mol) of $C_8H_{17}O(C_4H_8O)(C_3H_6O)(C_2H_4O)_2H$. The alcohol was heated at 75° C, and there was then added 2 grams of stannic chloride and 101 grams (1.1 mol) of epichlorohydrin over a period of about 1 hour. The temperature was then raised to 125° C, with continued stirring, and the mixture held at this temperature for 2 hours. Residual epichlorohydrin was then removed by vacuum distillation. The residual product was a slightly yellow liquid.

To 440 grams of this product there was added 340 g of a 40% aqueous solution of dimethylamine, corresponding to 3 mols of dimethylamine. The resulting mixture was then heated to 150° C in an autoclave with stirring, and held at this temperature for 1 hour. The reaction mixture was then cooled, and 40 grams (1 mol) of sodium hydroxide was added. The mixture was allowed to separate in a separatory funnel and the top phase containing the amine removed. Excess dimethylamine was then separated by vacuum distillation at 50° C. The product obtained was octyl mono oxybutylene monooxypropylene dioxy ethylene oxy-2-hydroxypropylene dimethylamine.

One part by weight of this product corresponding to 0.5 mol tertiary amine was stirred into 0.5 part by weight diethylene glycol and one part by weight of water. The mixture was heated to 70° C, and 0.6 mol monochloroacetic acid added at 70° C over 1 hour in the form of a 40% water solution neutralized with sodium hydroxide to pH 7. The reaction was allowed to proceed at 70° C for another hour, and was then continued for another 2 hours at 90° C. At the end of the reaction the product was a clear aqueous solution showing good cleaning properties of ampholytic betaine having the formula:

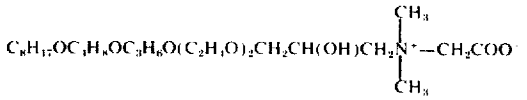

The yield calculated on the amount of added alcohol was 95%.

Having regard to the foregoing disclosure, the following is claimed as the inventive and patentable embodiments thereof:

1. An ampholytic betaine having the formula:

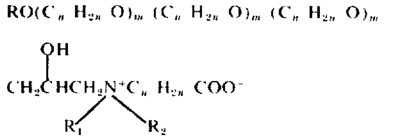

wherein

1. R is selected from the group consisting of alkyl, alkenyl, alkadienyl, alkatrienyl, and cycloalkyl groups having from about six to about twenty-two carbon atoms and alkyl phenyl and alkyl naphthyl groups linked to the oxygen of the OR group via a crabon of the phenyl or naphthyl nucleus and having from one to six alkyl groups, totalling from about four to about eighteen carbon atoms in the alkyl groups, each alkyl group having from one to about eighteen carbon atoms;

2. $R_1$ and $R_2$ are selected from the group consisting of alkyl groups having from one to about three carbon atoms;
3. $n_1$, $n_2$ and $n_3$ represent the number of carbon atoms in each unit, and are within the range from 2 to 4;
4 $m_1$, $m_2$ and $m_3$ represent the number of oxyalkylene units, and are within the range from 0 to 10, at least one of $m_1$, $m_2$ and $m_3$ is at least 1, and the sum of $m_1$, $m_2$ and $m_3$ is within the range from 1 to 10; and
5 $n_4$ represents the number of carbon atoms in the unit, and is within the range from 1 to 4.

2. An ampholytic betaine according to claim 1, in which $n_4$ is 1, so that both the nitrogen atom and the carboxylic group of the betaine are linked to a single carbon atom.

3. An ampholytic betaine according to claim 1, in which $n_1$, $n_2$ and $n_3$ are 2 and at least one of $m_1$, $m_2$ and $m_3$ is 1 or 2.

4. An ampholytic betain according to claim 1, in which $m_1$, $m_2$ and $m_3$ are 1.

5. An ampholytic betaine according to claim 1, in which R is alkyl or alkenyl.

6. An ampholytic betaine according to claim 1, in which R is cycloalkyl.

7. An ampholytic betain according to claim 1, in which R is alkyl substituted phenyl or naphthyl.

8. An ampholytic betaine according to claim 1, in which the oxyalkylene units include oxyethylene.

9. An ampholytic betaine according to claim 1, in which the oxyalkylene units include oxypropylene.

10. An ampholytic betaine according to claim 1, in which the oxyalkylene units include oxybutylene.

11. An ampholytic betaine according to claim 1, in which $R_1$ and $R_2$ are each methyl and $n_4$ is 1.

* * * * *